US00PP24676P2

(12) United States Plant Patent
Koppe

(10) Patent No.: US PP24,676 P2
(45) Date of Patent: Jul. 22, 2014

(54) ***BEGONIA* PLANT NAMED 'KRSSUSA01'**

(50) Latin Name: *Begonia×hiemalis*
Varietal Denomination: KRSSUSA01

(75) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 77 days.

(21) Appl. No.: 13/573,164

(22) Filed: Aug. 27, 2012

(51) Int. Cl.
*A01H 5/00* (2006.01)

(52) U.S. Cl.
USPC ..... Plt./347; Plt./343; Plt./344

(58) Field of Classification Search
USPC ..... Plt./343, 344, 347
See application file for complete search history.

*Primary Examiner* — Susan McCormick Ewoldt
(74) *Attorney, Agent, or Firm* — C. A. Whealy

(57) ABSTRACT

A new and distinct cultivar of *Begonia* plant named 'KRSSUSA01' characterized by its compact, upright, outwardly spreading and mounded plant habit; freely branching habit; dark green-colored leaves; numerous large salmon red-colored flowers with lighter red-colored centers that are held above and beyond the foliar plane; and excellent postproduction longevity.

2 Drawing Sheets

Botanical designation: *Begonia×hiemalis.*
Cultivar denomination: 'KRSSUSA01'.

CROSS REFERENCED TO CLOSELY-RELATED APPLICATIONS

Title: *Begonia* Plant Named 'KRSSUCO01'.
Applicant: Lubbertus H. Koppe.
Filed: Concurrently with this application U.S. Plant application Ser. No. 13/573,166.

BACKGROUND OF THE INVENTION

The present invention relates to a new and distinct cultivar of *Begonia* plant, botanically known as *Begonia×hiemalis,* commercially known as Elatior *Begonia* and hereinafter referred to by the name 'KRSSUSA01'.

The new *Begonia* plant is a naturally-occurring whole plant mutation of a proprietary selection of *Begonia×hiemalis* identified as code number KV03-0205-02, not patented. The new *Begonia* plant was discovered and selected by the Inventor as a single flowering plant from within a population of plants of the parent selection in a controlled greenhouse environment in Ermelo, The Netherlands in August, 2010.

Asexual reproduction of the new *Begonia* plant by vegetative cuttings taken in a controlled greenhouse environment in Ermelo, The Netherlands since November, 2010 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRSSUSA01'. These characteristics in combination distinguish 'KRSSUSA01' as a new and distinct *Begonia* plant:

1. Compact, upright, outwardly spreading and mounded plant habit.
2. Freely branching habit.
3. Dark green-colored leaves.
4. Numerous large salmon red-colored flowers with lighter-colored centers that are held above and beyond the foliar plane.
5. Excellent postproduction longevity.

Plants of the new *Begonia* differ primarily from plants of the parent selection in flower color. Plants of the new *Begonia* have salmon red-colored flowers whereas plants of the parent selection have dark pink-colored flowers. In addition, plants of the new *Begonia* have shorter internodes than plants of the parent selection.

Plants of the new *Begonia* can be compared to plants of the *Begonia* 'KRSSUCO01', U.S. Plant Patent application Ser. No. 13/573,166, filed concurrently. Plants of the new *Begonia* differ primarily from plants of 'KRSSUCO01' in flower color as plants of the new *Begonia* have salmon red-colored flowers whereas plants of 'KRSSUCO01' have coral red-colored flowers. In addition, plants of the new *Begonia* have longer leaf petioles than plants of 'KRSSUCO01'.

Plants of the new *Begonia* can be compared to plants of *Begonia×hiemalis* 'KRSSUWH01', disclosed in U.S. Plant Pat. No. 23,205. In side-by-side comparisons conducted in Ermelo, The Netherlands, plants of the new *Begonia* differed primarily from plants of 'KRSSUWH01' in flower color as plants of 'KRSSUWH01' had white-colored flowers.

Plants of the new *Begonia* can also be compared to plants of *Begonia×hiemalis* 'Dark Britt', not patented. In side-by-side comparisons conducted in Ermelo, The Netherlands, plants of the new *Begonia* differed primarily from plants of 'Dark Britt' in flower color as plants of 'Dark Britt' had orange-colored flowers. In addition, flowers of plants of the new *Begonia* had fewer tepaloids than flowers of plants of 'Dark Britt'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'KRSSUSA01' grown in a container.

The photograph on the second sheet are close up views of the upper and lower surfaces of typical leaves (right) and upper, lateral and lower surfaces of developing and open flowers of 'KRSSUSA01' (left).

DETAILED BOTANICAL DESCRIPTION

The aforementioned photographs and following observations and measurements describe plants grown during the spring in 13-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were pinched one time and were ten weeks old when the photographs and description were taken. In the following description, color references are made to The Royal Horticultural Society Colour Chart, 2007 Edition, except where general terms of ordinary dictionary significance are used.

Botanical classification: *Begonia×hiemalis* 'KRSSUSA01'.

Commercial classification: Elatior *Begonia*.

Parentage: Naturally-occurring whole plant mutation of a proprietary selection of *Begonia×hiemalis* identified as code number KV03-0205-02, not patented.

Propagation:

*Type.*—By terminal vegetative cuttings.

*Time to develop roots.*—About 20 days at temperatures of 20° C.

*Time to produce a rooted young plant.*—About five weeks at temperatures of 20° C.

*Root description.*—Fine, fibrous; white to orange brown in color.

*Rooting habit.*—Freely branching; medium density; plants of the new *Begonia* have not been observed to form tubers.

Plant description:

*Plant habit and form.*—Compact, upright, outwardly spreading and mounded plant habit; overall plant shape roughly globular; flowers held above and beyond the foliar plane.

*Growth habit.*—Moderately vigorous growth habit and moderate growth rate; suitable for 12-cm and larger containers; under optimal environmental and cultural conditions, usually about ten weeks are required to produce proportional 13-cm potted plants from cuttings; vegetative shoots are formed at basal nodes and flowering shoots are formed at upper nodes.

*Branching habit.*—Freely branching habit; when pinched, about eight lateral branches develop.

*Plant height.*—About 28 cm.

*Plant width.*—About 34.8 cm.

*Lateral branches.*—Length: About 11.9 cm. Diameter: About 9 mm. Internode length: About 2.4 cm. Angle: About 40° from vertical. Texture: Smooth, sparsely pubescent. Color, developing: Close to 144B to 144C. Color, fully developed: Between 144A and 146B.

*Leaves.*—Arrangement: Alternate; simple. Length: About 13.7 cm. Width: About 11.3 cm. Shape: Broadly ovate. Apex: Acute. Base: Oblique. Margin: Bi-serrate; laciniate. Texture, upper surface: Smooth, glabrous; velvety. Texture, lower surface: Smooth, glabrous. Venation pattern: Palmate. Color: Developing leaves, upper surface: Between N137A and 147A. Developing leaves, lower surface: Close to 146C. Fully expanded leaves, upper surface: Darker than between 147A and N189A; venation, close to 143A. Fully expanded leaves, lower surface: Close to 191A tinged with close to 182A; venation, close to 144A. Petioles: Length: About 10.6 cm. Diameter: About 5 mm. Texture, upper and lower surfaces: Sparsely pubescent. Color, upper surface: Close to 144B; at leaf attachment, close to 173A. Color, lower surface: Close to 144B; at leaf attachment, close to 173B. Stipules: Length: About 1 cm. Width: About 1.1 cm. Shape: Broadly ovate. Margin: Entire. Texture, upper and lower surfaces: Smooth, glabrous. Color, upper and lower surfaces: Close to 180C; venation, close to 180A.

Flower description:

*Flower form and flowering habit.*—Large semi-double rotate flowers arranged in axillary compound cymes; usually about five flowers per cyme, numerous cymes in flower simultaneously and about 150 flowers developing per plant; flowers face upright to outwardly and are positioned above and beyond the foliar plane.

*Natural flowering season.*—Plants begin flowering about six weeks after pinching; plants flower continuously year round regardless of nyctoperiod, however plants are more freely flowering from autumn to spring.

*Flower longevity.*—Individual flowers last about ten days on the plant; flowers not persistent; flowering plants have excellent postproduction longevity and typical maintain good substance for about six weeks under interior conditions.

*Fragrance.*—None detected.

*Inflorescence height.*—About 14.7 cm.

*Inflorescence diameter.*—About 11.1 cm.

*Flower buds.*—Length: About 2 cm. Diameter: Ranging from about 7 mm to 17 mm. Shape: Reniform, flattened. Color: Close to 44D.

*Flowers.*—Shape: Rotate; semi-double. Diameter: About 7.8 cm. Depth (height): About 2.8 cm.

*Tepals.*—Quantity per flower: About four arranged in a single whorl. Length: About 3.9 cm. Width: About 4.7 cm. Shape: Roughly orbicular. Apex: Rounded. Margin: Entire. Texture, upper surface: Smooth, glabrous; slightly velvety. Texture, lower surface: Smooth, glabrous. Color: When opening, upper surface: Between N30A and 33B. When opening, lower surface: Close to 41B. Fully opened, upper surface: Close to 40B to 40C; towards the base, close to 48C; with development, color becoming closer to 41D. Fully opened, lower surface: Close to 40C and 41C; with development, color becoming closer to 41D.

*Tepaloids.*—Quantity per flower: About ten arranged in several whorls. Length: About 2.9 cm. Width: About 2.3 cm. Shape: Broadly elliptic to obovate. Apex: Rounded. Margin: Entire. Texture, upper and lower surfaces: Smooth, glabrous; slightly velvety. Color: When opening, upper surface: Between N30A and 33B. When opening, lower surface: Close to 41B. Fully opened, upper surface: Close to 40B to 40C; towards the base, close to 48C; with development, color becoming closer to 41D. Fully opened, lower surface: Close to 40C and 41C; with development, color becoming closer to 41D.

*Peduncles.*—Length: About 6.8 cm. Diameter: About 5 mm. Angle: About 50° from lateral branch axis. Texture: Smooth, glabrous. Color: Close to 199A.

*Pedicels.*—Length: About 3.1 cm. Diameter: About 2 mm. Angle: About 35° from peduncle axis. Texture: Smooth, glabrous. Color: Close to 172B.

*Reproductive organs.*—Stamens: Quantity per flower: About 50. Filament length: About 5 mm. Filament color: Close to 13B. Anther shape: Club-shaped; basifixed. Anther length: About 2 mm. Anther color: Close to 13B. Pollen amount: None observed. Pistils: None observed.

*Seeds and fruits.*—Seed and fruit development have not been observed on plants of the new *Begonia*.

Disease & pest resistance: Resistance to pathogens and pests common to *Begonia* has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'KRSSUSA01' as illustrated and described.

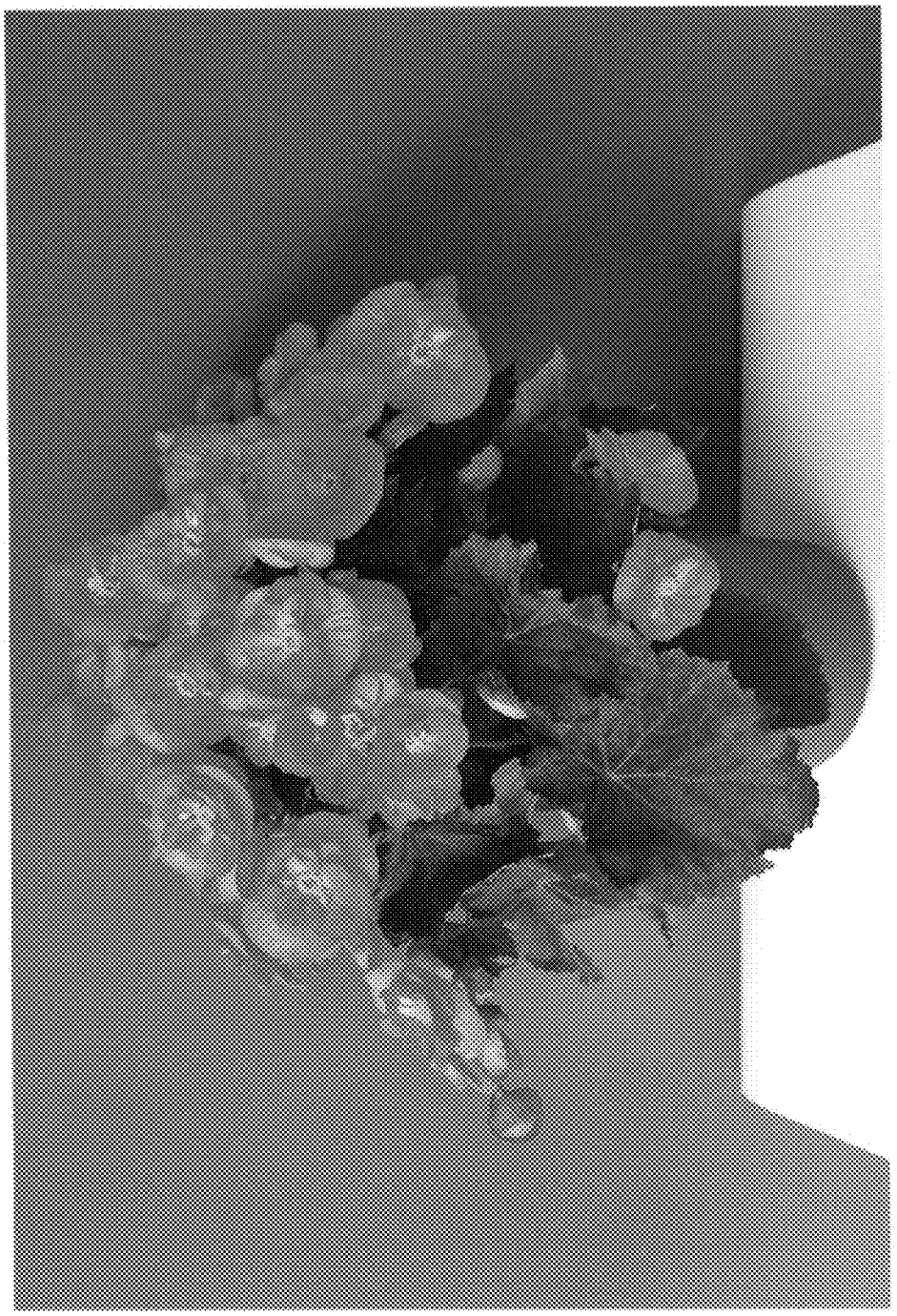

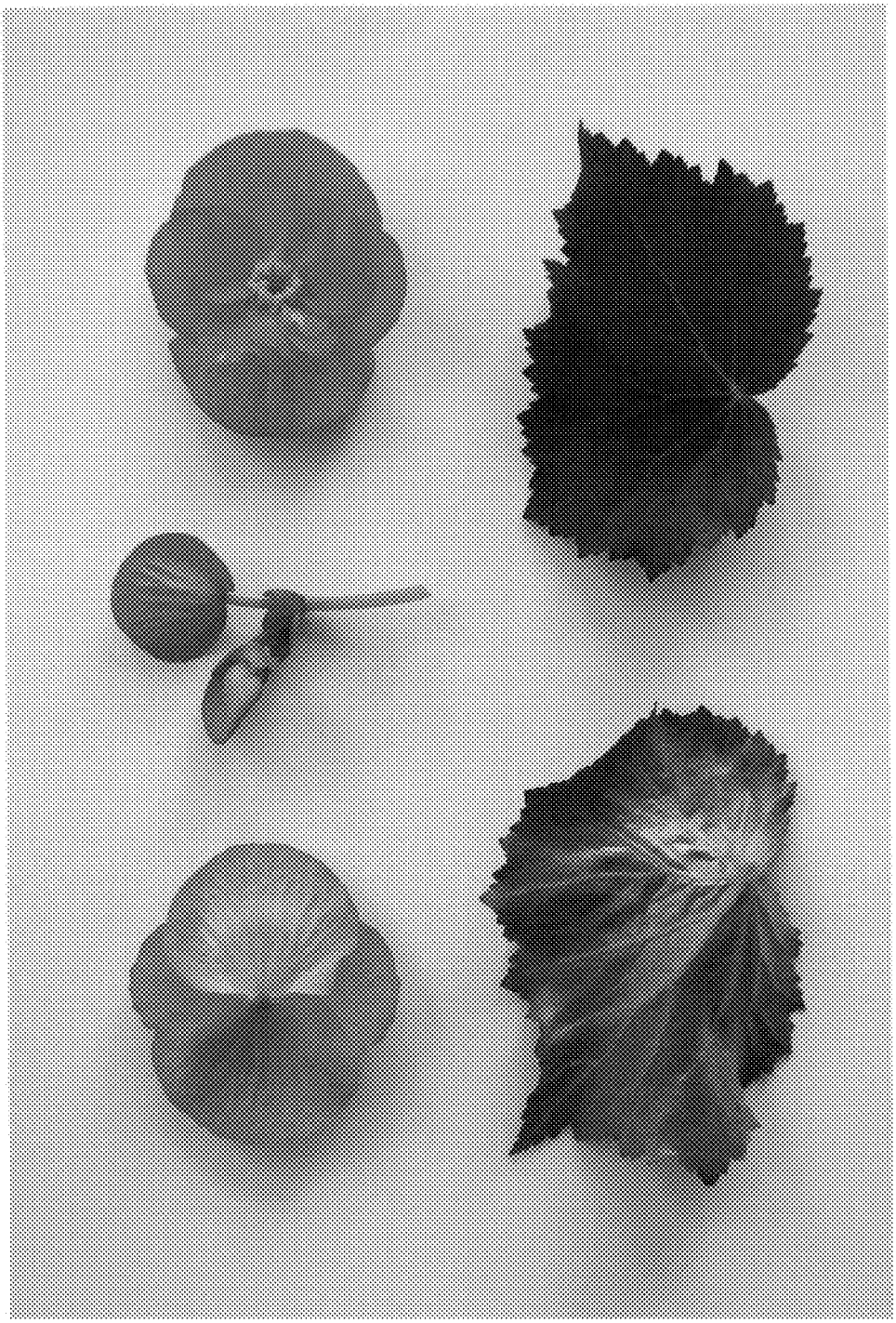

* * * * *